United States Patent [19]

Bauman

[11] Patent Number: 4,729,367
[45] Date of Patent: Mar. 8, 1988

[54] SUBMERGIBLE LARYNGOSCOPE WITH HANDLE FLUID SEALING MEANS

[76] Inventor: Jack Bauman, 16677 San Onofre, Pacific Palisades, Calif. 90272

[21] Appl. No.: 3,174

[22] Filed: Jan. 27, 1987

Related U.S. Application Data

[63] Continuation-in-part of Ser. No. 830,280, Feb. 18, 1986, Pat. No. 4,669,449.

[51] Int. Cl.[4] .............................................. A61B 1/06
[52] U.S. Cl. ..................................................... 128/11
[58] Field of Search ................ 128/6, 10, 11; 362/118, 362/158, 202; 179/111 E

[56] References Cited

U.S. PATENT DOCUMENTS

| | | |
|---|---|---|
| 1,165,232 | 12/1915 | De Zeng . |
| 2,289,226 | 7/1942 | Foregger . |
| 2,433,705 | 12/1947 | Palmeter . |
| 3,295,514 | 1/1967 | Hein et al. . |
| 3,426,749 | 2/1969 | Jephcott . |
| 3,579,269 | 5/1971 | Ostensen . |
| 3,592,199 | 7/1971 | Ostensen . |
| 3,598,113 | 9/1971 | Moore . |
| 3,609,340 | 9/1971 | Habro . |
| 3,766,909 | 10/1973 | Ozbey . |
| 3,771,514 | 11/1973 | Huffman et al. . |
| 3,826,248 | 7/1974 | Gobels . |
| 3,986,854 | 10/1976 | Scrivo et al. . |
| 4,037,588 | 7/1977 | Heckele . |
| 4,112,933 | 9/1978 | Moses . |
| 4,114,609 | 9/1977 | Moses . |
| 4,273,112 | 6/1981 | Heine et al. . |
| 4,295,465 | 10/1981 | Racz et al. . |
| 4,306,547 | 12/1981 | Lowell . |
| 4,314,551 | 2/1982 | Kadell . |
| 4,320,745 | 3/1982 | Bhitiyakul et al. . |
| 4,337,761 | 7/1982 | Upsher . |
| 4,384,570 | 5/1983 | Roberts . |
| 4,436,648 | 3/1984 | Khanna et al. . |
| 4,437,458 | 3/1984 | Upsher . |
| 4,527,223 | 7/1985 | Maglica . |
| 4,556,052 | 12/1985 | Muller . |

Primary Examiner—Max Hindenburg
Attorney, Agent, or Firm—William W. Haefliger

[57] ABSTRACT

A fluid submersible laryngoscope includes a hollow handle to contain a power supply such as dry cell means. A light source is carried by the handle, and structure is provided to place that power supply in electrical energy transmitting relation with that light source to direct light into transmitting means carried by the blade. The blade is insertible into a patient's mouth to illuminate the throat area. Sealing structure is provided between the terminal light source and handle to block access of external fluid into the hollow handle proximate the light source whether or not the blade is attached to the handle, and when the handle is submerged in fluid.

13 Claims, 11 Drawing Figures

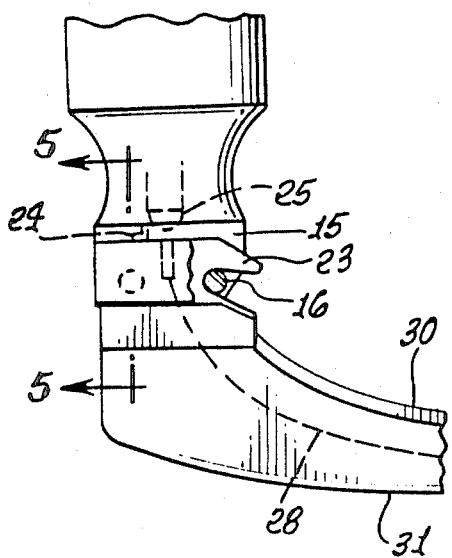
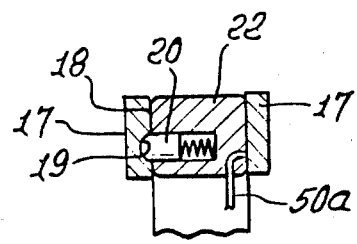
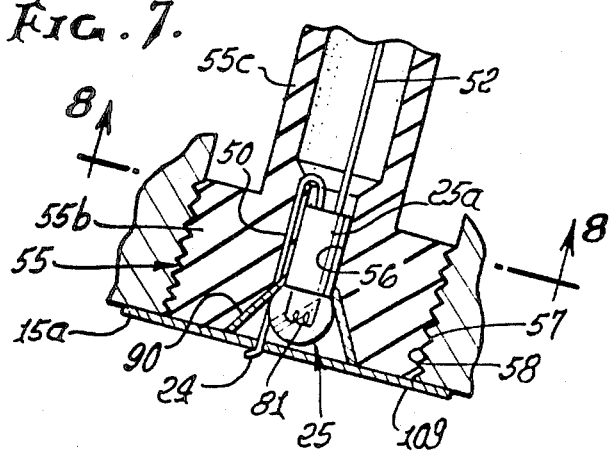
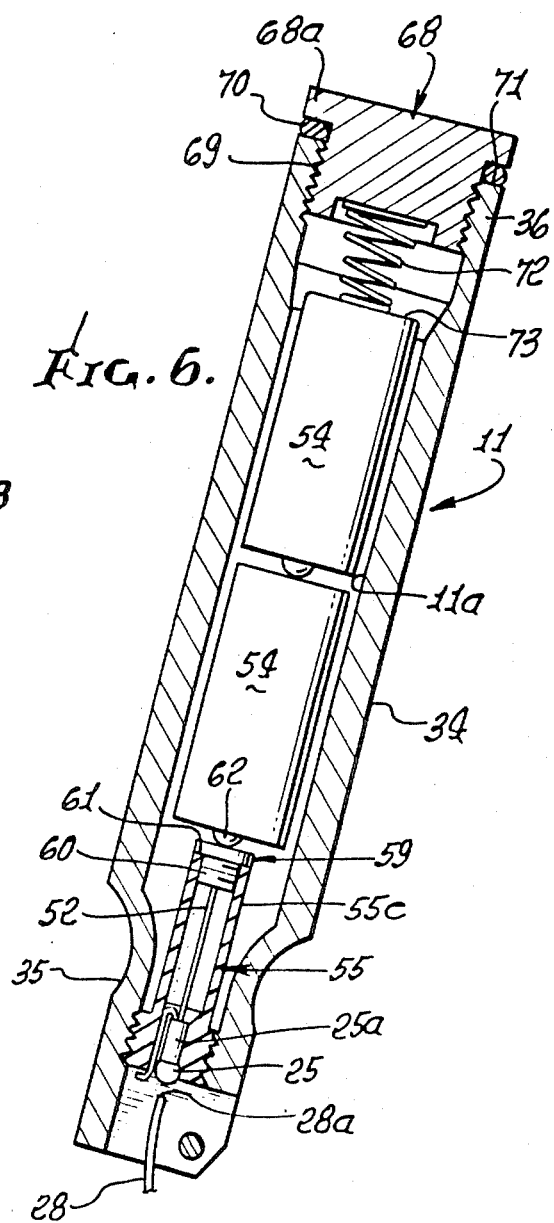
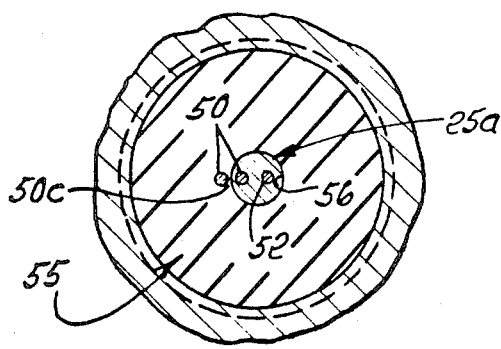

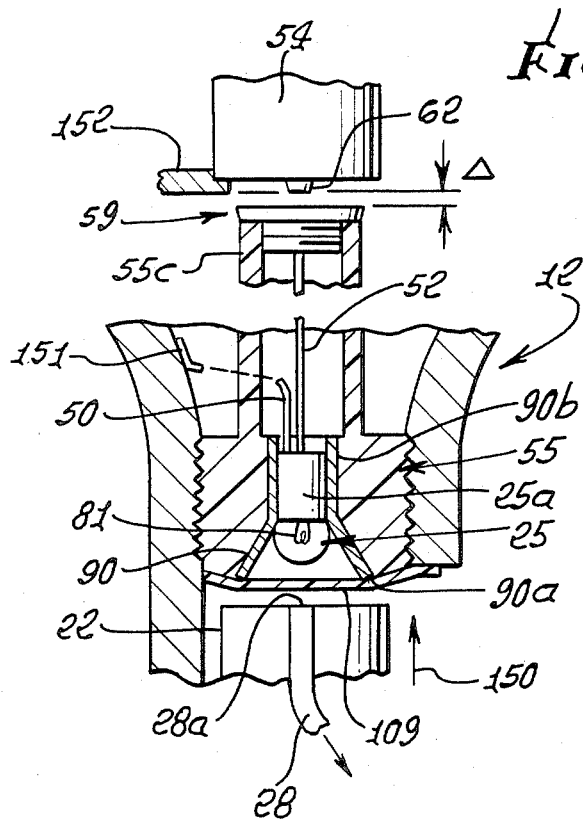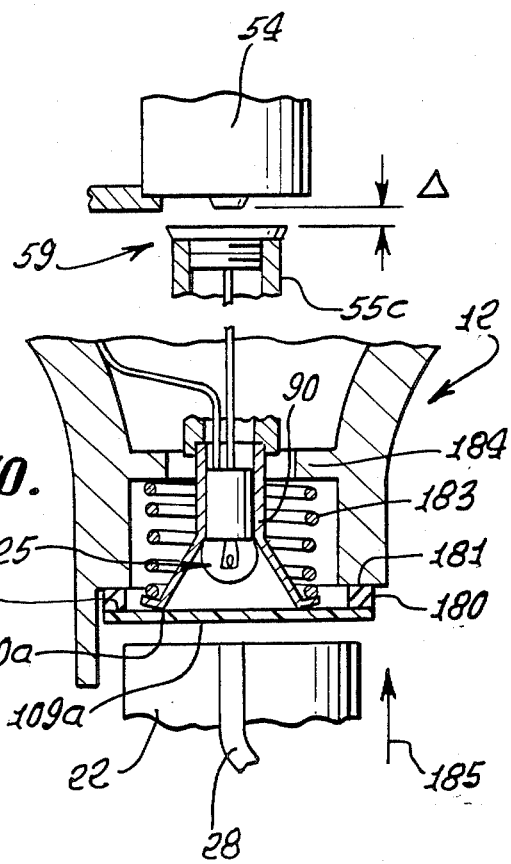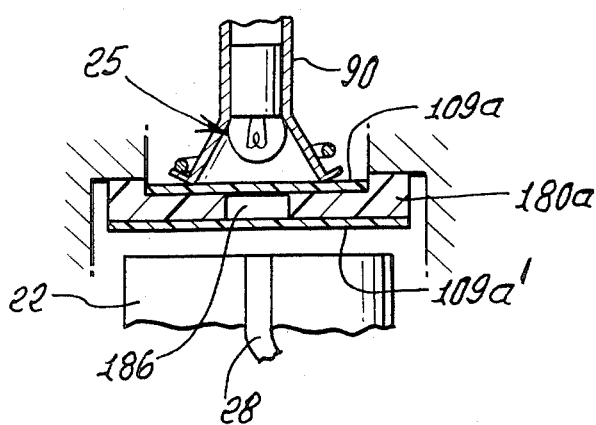

SUBMERGIBLE LARYNGOSCOPE WITH HANDLE FLUID SEALING MEANS

This application is a continuation-in-part of Ser. No. 830,280, filed Feb. 18, 1986, now U.S. Pat. No. 4,669,449, issued June 6, 1987.

BACKGROUND OF THE INVENTION

This invention generally relates to examining devices such as laryngoscopes and particularly to an improved submersible device of this type.

Laryngoscopes generally comprise a blade and a cooperating handle which are connected together in an L-shaped configuration. The hollow handle normally serves as an enclosure for a power supply such as one or more dry cells which are adapted to energize a light bulb. The light from the bulb passes to the distal end of the blade to illuminate the patient's mouth and larynx during the examination thereof by medical personnel. A surface on the blade is used to press against the tongue and mandible of a patient in a supine position in order to prevent the patient's tongue from obstructing the visual examination of the larynx by medical personnel.

While the instrument is useful for examining the larynx, the primary function of the laryngoscope is to expose the larynx in order to facilitate the insertion of an endotracheal tube. The surface of the laryngoscope blade adjacent the handle is urged against the tongue and mandible to expose the larynx in such procedures and the opposite blade surface is positioned opposing the upper front teeth of the patient.

It becomes desirable to provide a re-usable blade and handle which then must be cleaned thoroughly after use since fluid from the patient's mouth area can contaminate the handle. However, washing of the handle presents the problem of fluid gaining access to the power supply, i.e. dry cells, within the handle hollow, as via one or both ends of the handle. This a particular problem when the light bulb is carried at the end of the handle to which the blade attaches, as cleaning fluid can leak past the bulb into the handle to cause bulb circuit malfunction.

SUMMARY OF THE INVENTION

It is a major object of the invention to provide a solution to the above problem, through provision of a fluid or liquid submersible laryngoscope including a hollow handle to contain power supply means, a blade to be inserted into a patient's mouth, and means to removably attach the blade to an end portion of the handle in a substantially L-shape configuration, the improvement comprising:

(a) a light source carried by the handle at said handle end portion,
(b) means to place the light source in electrically energizing relation with the power supply means, and when the blade is attached to the handle, to direct light into light transmitting means carried by the blade,
(c) and first fluid sealing means between the light source and handle to block access of external fluid into the handle proximate the light source whether or not the blade is attached to the handle, and when the handle is submerged in fluid.

As will appear, the fluid sealing means typically comprises a tubular elastomeric body carrying said light source, the light source having a shank in fluid sealing engagement with a bore defined by said elastomeric body, said body having an exterior generally annular surface in fluid sealing engagement with a bore defined by the handle. Further, the light source may have two terminals, one of which extends lengthwise within said body toward the power source, for electrical connection therewith, and the other of which extend toward the blade to establish electrical connection therewith when the blade is detachably secured to the handle; and an end closure may be attached to an end of the body remote from the light source, said closure providing a current passing connection between the power source and said one terminal. Further, a reflector may be intergrated with the tubular elastomeric body, proximate the light source. In this regard, the elastomeric body surface and handle bore preferably have tight, compressed, threaded interconnection to establish a very tight seal therebetween.

The fluid sealing means may also include a transparent layer of material extending across a zone through which light is transmitted by the light source and reflector at said end portion of the handle; and/or, the fluid sealing means may include resiliently compressible material to be compressed by the blade when the light source and reflector are displaced relatively toward the power supply means.

Also, an end cap may be removably attached to the end of the handle remote from said blade, and second fluid sealing means between the cap and handle blocks access of external fluid into the hollow handle. In this regard, the handle and end cap are typically metallic, and the second fluid sealing means comprises an elastomeric O-ring. The blade itself is typically metallic and may carry the light bulb.

These and other features and advantages of the invention will become more apparent from the following detailed description when taken in conjunction with the accompanying drawing:

BRIEF DESCRIPTION OF THE DRAWINGS

FIG. 4 is partial side elevational view partially in section, of the laryngoscope with the blade in the operative position;

FIG. 5 is a cross sectional view taken along the lines of 5—5 shown in FIG. 4;

FIG. 6 is a cross sectional view of the handle;

FIG. 7 is an enlarged view of light bulb mounting;

FIG. 8 is a section on lines 8—8 of FIG. 7;

FIGS. 9 and 10 are fragmentary sections, like FIG. 7, showing modifications; and FIG. 11 is another fragmentary view showing a further modification.

DETAILED DESCRIPTION OF THE INVENTION

Figure 1:
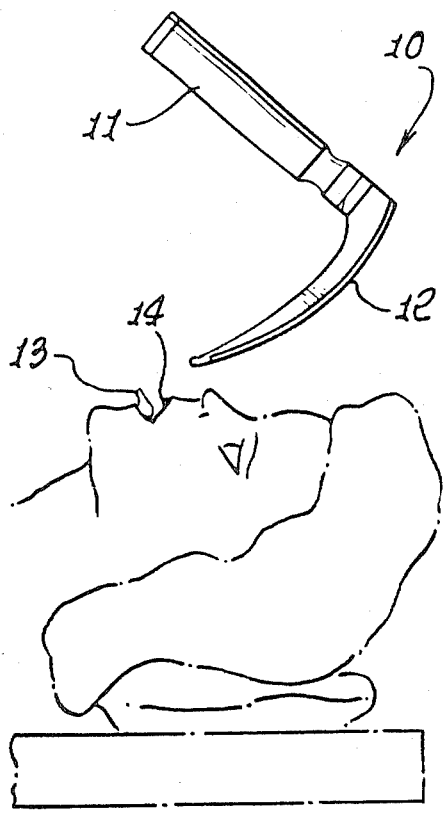
FIG. 1 is a side elevational view of a laryngoscope preparatory to being used on a patient which embodies features of the invention.

Reference is made to the drawings which illustrate a laryngoscope embodying features of the present invention. The instrument is intended for use by medical personnel in the examination of a patient's mouth and larynx and particularly to expose the larynx to facilitate the insertion of an endotracheal tube. As shown in FIG.

1, the laryngoscope 10, which comprises a handle 11 and blade 12, is utilized to depress the patient's tongue and mandible 13. Frequently, the patient's front teeth 14 are used as a fulcrum for the blade 12 in order to more completely expose the patient's larynx during the examination of the larynx and the insertion of an endotracheal tube.

One form of means used to couple the blade 11 to the handle 12 is illustrated in FIGS. 2–6. As shown therein, the upper end of the handle 11 has an open channel 15, which is provided with a pivot rod 16 extending between flanges 17. The inner side of one flange has a groove or dimple 19 adapted to seat a spring urged detent 20 projecting at one side surface 18 of a boot-shaped appendage 22 on the blade.

The boot shaped appendage 22 interfits into the open channel 15 and is mounted therein in a pivotal fashion. The front end 23 of the boot shaped appendage 22 is hooked under the pivot rod 16 during the pivotal mounting thereof, in a conventional fashion. To mount the blade onto the handle 11, the appendage 22 of the blade 12 is inserted into the open top channel 15 with a pivotal motion so that the front end 23 rotates under the pivot rod 16 i.e., from FIG. 3 to FIG. 4 condition. The detent 20 moves into engagement with the groove 19 provided in the surface 18, to thereby snap-retain the appendage 22 in firm interfit with the channel and pivot rod 16, as the blade moves from ready position, as shown in FIG. 3, to fixed position seen in FIG. 4.

Preferably, a light switch or contact 24 is provided at the bottom of the channel 15 in a position so that it is activated only when the blade 12 is rotated and locked into an operating position. A light source 25 such as an incandescent bulb is provided proximate the channel 15 and is energized when the light switch 24 is activated. As shown in FIG. 3, when the blade 12 is initially mounted on the handle 11, the blade 11 is in a ready position on the handle 12 but the bottom surface 26 of the appendage 22 does not activate, i.e. engage, the light switch. Further rotation of the blade 12 causes the detent 20 to engage the groove 19, and to thereby, lock the blade 12 in an operating position and simultaneously therewith to cause metallic bottom surface 26 to engage, i.e. activate the light switch 24, which in turn energizes the light source 25. Wire 50 extends from switch 24 to the bulb, and that wire may be the bulb terminal wire the end of which defines switch 24. See FIG. 7.

Figure 2:
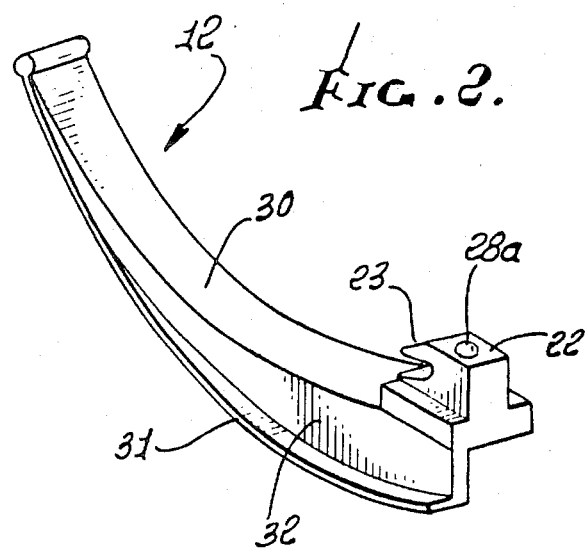
FIG. 2 is a perspective exploded view of the blade of the laryngoscope shown in FIG. 1.
Figure 3:
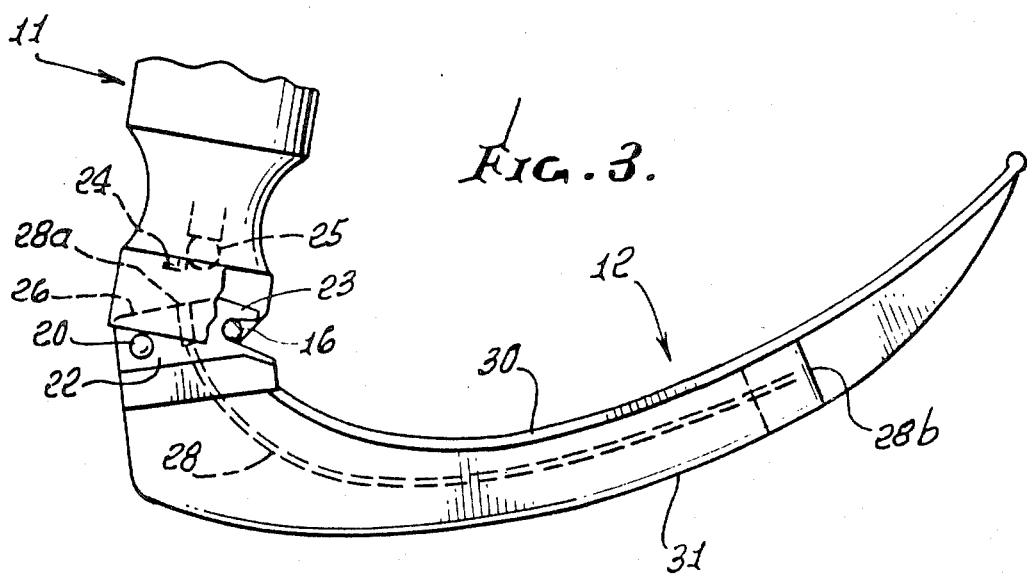
FIG. 3 is a side elevational view partially in section, of the laryngoscope with the blade in a ready position.

As best shown in FIGS. 2–4, light is directed from the light source 25 to ensure the proper illumination of a patient's mouth and larynx when the laryngoscope is being used. The light source or bulb 25 is located at the bottom wall 15a of channel 15 so that, when the blade 12 is rotated into its final operating position, not only is switch 24 engaged, but also the energized bulb directs light into the end 28a of the light pipe or duct 28 carried by the blade and conducting light to the light emitting end 28b directing light forwardly from a channel in blade web 32. Duct 28 may be of optical fiber.

The lower portion 30 of the blade 12 which comes in contact with the tongue and mandible 13 of the patient should be rigid, whereas the upper section 31 comes in contact with the patient's teeth 14. The surface 31 which is in contact with the patient's teeth 14 is supported to the rigid portion 30 of the blade 12 by means of wall or web 32. Blade 12 typically metallic. Duct 28 is protectively received in a metal channel extending along the web 32.

The handle 11, which is typically metallic has an internal cavity 11a which is adapted to hold one or more battery units 54(see FIG. 6) which supply electrical energy to light source 25. The handle comprises a tubular body 34 having a reduced diameter end 35, and an opposite end 36. The exposed contact 24 is advantageously formed at the end of light bulb terminal wire located at handle end 35. The light bulb is electrically energized when the metal surface 26 of the blade engages contact 24 in FIG. 4 position of the blade.

Also provided is first fluid sealing means located between the bulb and handle to block access of external fluid into the hollow handle, whether or not the blade is attached to the handle, and when the handle is submerged in fluid as during cleaning. As shown, the first fluid sealing means comprises a tubular elastomeric body 55 carrying the light bulb, the bulb having a shank 25a in fluid sealing relation with a bore 56 defined by the elastomeric body 55, the latter also having an exterior generally annular surface 57 in fluid sealing engagement with a bore 58 defined by the handle. Surfaces 57 and 58 may advantageously be threaded, and be in tight compressive engagement to define a good fluid seal. An elliptical reflector 90 is provided on body 55, as shown, to reflect bulb light to 28a and to provide a bulb recess. The bulb and reflector are covered by a transparent window 109, to seal them off from the exterior, and also provide a sealed beam unit.

Also shown is an end closure 59 attached as by threading 60 to an end 61 of said body remote from the terminal 24, said closure providing a current passing connection between the power source and said pin. Note that dry cell terminal 62 engages conductive metallic closure 59, which is carried on the insulative body 57.

The head 55b of body 55 is enlarged to provide a firm mount for the bulb 25 and the reduced diameter extent 55c of the body which mounts closure 59, so that elastomeric shank 55c can withstand loading imposed by the batteries 54.

An annular end cap 68 is removably attached to the end 36 of the handle, remote from the blade, and second fluid sealing means is provided between the cap and handle, to block access of external fluid into the hollow handle, via end 36. In this regard, the cap may have threaded attachment at 69 to the handle, the cap and handle are typically metallic. Said second fluid sealing means may comprise an elastomeric O-ring 70 compressed between cap flange 68a and handle end 71. A coil spring 72 is located between the cap 68 and the end 73 of one battery 54, to establish a ground.

The second terminal wire 52 of the light bulb extends lengthwise within the body 55 toward the power sources, for electrical connection with conductive metallic end closure, when the blade is secured to the handle. Current then passes from the batteries 54 via closure 59 terminal wire 52 to the bulb wire 81, then via terminal wire 50, the metallic blade and handle, and the conductive spring 72 to the battery base 73. Note that wire 50 is tightly compressed by body 55b, in a channel 50c, to maintain the seal.

After use, the blade is decoupled from the handle by simple rotating the blade 12 toward the handle 11 and then pushing upwardly on the blade 12 to disengage or unhook the front end 12 of appendage 22 from the pivot rod 16. The blade being formed from metal, can be sterilized and reused, as is the handle.

Referring now to FIG. 9, components like those of FIGS. 6 and 7 bear the same identifying numbers. Means is provided to place the light source 25 and 81 in electrically energizing relation with the power supply means, as at 54, when the blade is attached to the handle to displace the light source and reflector 90 relatively toward the power supply means. In the example, such means may be considered to include light bulb terminal wire 52 extending to metallic end closure or contact 59. When the blade appendage 22 transmits force via sheet 109 to the reflector annular lip or bead 90a, in the direction of arrow 150, the reflector, bulb, and closure 59 are displaced toward battery 54 through a distance Δ to cause contact 59 to engage the battery contact. This establishes a circuit as referred to above, to energize wire 81 in the bulb. Note also that the second terminal wire 50 associated with the bulb may make grounding contact with the handle, as at 151.

The yieldably resilient elastomeric body 55 normally urges the reflector and blade away from the battery to maintain spacing Δ between 59 and 62. Battery 54 is shown as engaging a locating ledge 152 associated with the handle. Alternatively, the contacts 59 and 62 may remain in engagement, and the terminal wire 50 may only engage the handle, to establish the energizing circuit, when the body 55 is displaced toward the battery as described.

The transparent strip 109 is adhesively sealed to the reflector lip or bead 90a, annularly, to at all times block access of fluid such as water to the interior of the handle via the bulb reflector whether or not the blade is attached to the handle, and whether or not the handle is submerged in fluid, as during cleaning. Note also the reflector tubular shank 90b positioning the bulb shank 25a. Transparent sheet 109 may consist of polycarbonate, for example, and extends across the zone through which light is transmitted by the bulb and reflector toward the end 28a of the optical light pipe 28.

The construction in FIG. 10 is similar; however, the fluid sealing means includes resiliently compressible material 180 extending annularly about the lip or bead 90a of the reflector and sealingly attached at 181 to the end of the handle, as shown. Transparent strip 109a extends across the end of the reflector, as before, and is sealingly attached at 182 to the resilient material 180. A compression spring 183 extends between lip 90a and a ledge 184, to resist inward deflection of the reflector and bulb. As blade appendage 22 moves in direction 185, its end 26 engages the strip 109a and the material 180 cushions the movement of the blade end 22 as the reflector, bulb and contact 59 are deflected, as before, to establish the circuit.

FIG. 11 is similar to FIG. 10, except in this case the resilient material 180a becomes compressed and transmits force from the blade appendage 22 to the reflector, to deflect the latter through amount Δ. Transparent strips or sheets 109a and 109a' extend across the opening 186 in material that transmits light from bulb 25 and reflector 90 to the light pipe 28. Those strips are sealingly attached to opposite sides of the material 180a, as shown; and material 180a is annularly sealed at 181 to the end of the handle.

Although the specific embodiment of the invention is described herein in connection with laryngoscopes, it is clear that the improved means to connect a blade and a handle into an L-shaped configuration can be employed in other examining devices.

Modifications and improvements can be made to the present invention without departing from the inventive concepts thereof. One modification is to make the blade of molded plastic (for throw away) with metallic coating particularly at areas to contact wire 24 and metallic pivot pin 16, to establish electrical communication therebetween.

Element 70 may be a rubber washer.

I claim:

1. In a fluid submersible laryngoscope including a hollow handle containing power supply means, a blade to be inserted into a patient's mouth, light transmitting means carried by the blade, and means to removably attach the blade to an end portion of the handle in a substantially L-shaped configuration, the improvement comprising:
   (a) a light source with a reflector carried by the handle at said handle end portion, for movement relative to the handle and power supply means,
   (b) means to place the light source in electrically energizing relation with the power supply means when the blade is attached to the handle to displace the light source relatively toward the power supply means, whereby light is directed into said light transmitting means carried by the handle,
   (c) and fluid sealing means blocking access of external fluid into the hollow handle proximate the light source and reflector, whether or not the blade is attached to the handle, and whether or not the handle is submerged in fluid,
   (d) said fluid sealing means extending outwardly at said end portion of the handle to be contacted by the blade when the blade is attached to the handle,
   (e) said fluid sealing means including resiliently compressible material to be compressed by the blade when the light source is displaced relatively toward said power supply means.

2. The improvement of claim 1 wherein said fluid sealing means includes a transparent layer of material extending across a zone through which light is transmitted by the light source at said end portion of the handle.

3. The improvement of claim 1 wherein said fluid sealing means includes a tubular elastomeric body extending about and carrying the light source and reflector for said movement thereof.

4. The improvement of claim 1 including a compression spring urging the reflector and light source relatively away from the power supply means, and adapted to be compressed when the light source and reflector are displaced by the blade.

5. The improvement of claim 1 wherein said fluid sealing means comprises a tubular elastomeric body carrying said light source, the light source having a shank in fluid sealing engagement with a bore defined by said elastomeric body, said body having an exterior generally annular surface in fluid sealing engagement with a bore defined by the handle.

6. The improvement of claim 5 wherein said body surface and handle bore have threaded interconnection.

7. The improvement of claim 1 wherein said means to place the light source in electrically energizing relation with the power supply means includes two terminals connected with the light source and one of which extends lengthwise within said handle toward the power source, for electrical connection therewith, and the other of which extends toward the blade to establish electrical connection therewith when the blade is detachably secured to the handle.

8. The improvement of claim 7 including an end closure attached to an end of the handle remote from the light source, said closure providing a current passing connection between the power source and said one terminal.

9. The improvement of claim 1 including an end cap removably attached to the end of the handle remote from this blade, and second fluid sealing means between the cap and handle to block access of external fluid into the hollow handle.

10. The improvement of claim 9 wherein the handle and cap are metallic and said second fluid sealing means comprises an elastomeric O-ring.

11. The improvement of claim 1 wherein the light transmitting means carried by the blade includes an optical fiber light duct having a terminal to receive light from the light source.

12. The improvement of claim 1 wherein the handle is metallic, and the blade is at least in part formed of molded plastic, and has metallic coating.

13. The improvement of claim 1 wherein said means to place the light source in electrically energizing relation with the power supply means includes two terminals one of which extends toward a switch in electrical connection with the power supply means, and the other of which extends toward an electrical connection with the handle, which is metallic.

* * * * *